(12) United States Patent
Namekawa et al.

(10) Patent No.: US 11,428,685 B2
(45) Date of Patent: Aug. 30, 2022

(54) METHOD OF ANALYZING RESINS ADHERING TO CRUSHED POLYSILICON

(71) Applicant: Tokuyama Corporation, Yamaguchi (JP)

(72) Inventors: Manato Namekawa, Yamaguchi (JP); Mikie Takemoto, Yamaguchi (JP)

(73) Assignee: Tokuyama Corporation, Yamaguchi (JP)

( * ) Notice: Subject to any disclaimer, the term of this patent is extended or adjusted under 35 U.S.C. 154(b) by 624 days.

(21) Appl. No.: 16/469,202

(22) PCT Filed: Dec. 14, 2017

(86) PCT No.: PCT/JP2017/044936
§ 371 (c)(1),
(2) Date: Jun. 13, 2019

(87) PCT Pub. No.: WO2018/110653
PCT Pub. Date: Jun. 21, 2018

(65) Prior Publication Data
US 2019/0391126 A1 Dec. 26, 2019

(30) Foreign Application Priority Data
Dec. 16, 2016 (JP) .............................. JP2016-244778

(51) Int. Cl.
| | | |
|---|---|---|
| *G01N 33/44* | (2006.01) | |
| *G01N 1/28* | (2006.01) | |
| *G01N 1/40* | (2006.01) | |
| *C08L 23/12* | (2006.01) | |
| *C08L 23/06* | (2006.01) | |
| *C08L 27/16* | (2006.01) | |
| *C08L 27/18* | (2006.01) | |
| *C08L 71/00* | (2006.01) | |
| *C08L 75/04* | (2006.01) | |

(52) U.S. Cl.
CPC .......... *G01N 33/442* (2013.01); *G01N 1/286* (2013.01); *G01N 1/4022* (2013.01); *C08L 23/06* (2013.01); *C08L 23/12* (2013.01); *C08L 27/16* (2013.01); *C08L 27/18* (2013.01); *C08L 71/00* (2013.01); *C08L 75/04* (2013.01)

(58) Field of Classification Search
CPC ...... G01N 33/442; G01N 33/00; G01N 1/286; G01N 1/4022; G01N 2030/128
See application file for complete search history.

(56) References Cited

U.S. PATENT DOCUMENTS

| | | |
|---|---|---|
| 4,525,336 A | 6/1985 | Griesshammer et al. |
| 5,242,671 A | 9/1993 | Allen et al. |
| 6,248,997 B1 | 6/2001 | Shiramizu |
| 10,307,763 B2 | 6/2019 | Kawaguchi et al. |
| 2013/0216466 A1 | 8/2013 | Traunspurger et al. |
| 2016/0339485 A1 | 11/2016 | Nishimura et al. |

FOREIGN PATENT DOCUMENTS

| | | |
|---|---|---|
| JP | 2000266650 A | 9/2000 |
| JP | 2013170122 A | 9/2013 |
| JP | 2016056066 A | 4/2016 |
| JP | 2016210637 A | 12/2016 |

OTHER PUBLICATIONS

English abstract of JP 2000266650 A, Sep. 29, 2000.
English abstract of JP 2013170122 A, Sep. 2, 2013.
English abstract of JP 2016056066 A, Apr. 21, 2016.
PCT International Preliminary Reporton Patentability, dated Jun. 2019.
Espacenet English Abstract for JP2016210637 A, printed on Oct. 14, 2020.
European Patent Office Extended Search Report, dated Jul. 30, 2020.
Fahong, L. et al., "Study on Staged Pyrolysis of Waste Plastic Mixture", Petroleum Processing and Petrochemicals, May 2001, Issue 5, vol. 32, 51-54.
English Abstract of Fahong, L. et al., "Study on Staged Pyrolysis of Waste Plastic Mixture", Petroleum Processing and Petrochemicals, May 2001, Issue 5, vol. 32, 51-54.

*Primary Examiner* — Christopher Adam Hixson
(74) *Attorney, Agent, or Firm* — Cahn & Samuels, LLP

(57) ABSTRACT

Provided is an analysis method capable of qualitatively determining resins adhering to crushed polysilicon with high sensitivity and further capable of quantitatively determining the resins with high precision. The analysis method comprises removing organic volatile components from crushed polysilicon by heating, then raising a temperature of the crushed polysilicon in a stream of an inert gas, collecting resin decomposition products produced at the heating temperature, and analyzing decomposition products unique to the resins, to thereby identify the types of the resins adhering to the crushed polysilicon. Moreover, it is also possible to prepare a standard curve regarding each of the decomposition products unique to the resins and to determine an adhesion quantity of each of the adhering resins based on the standard curve.

6 Claims, 2 Drawing Sheets

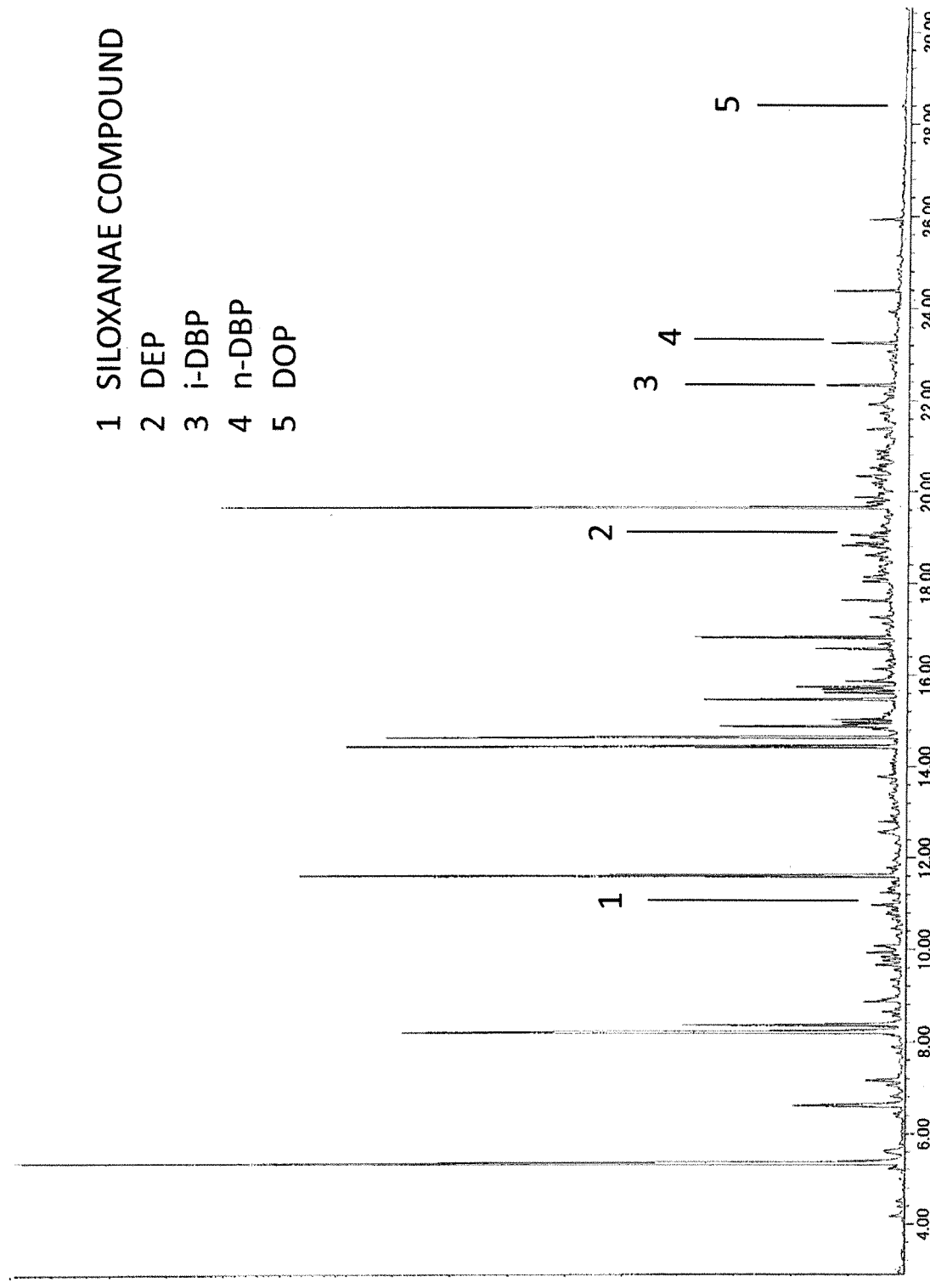

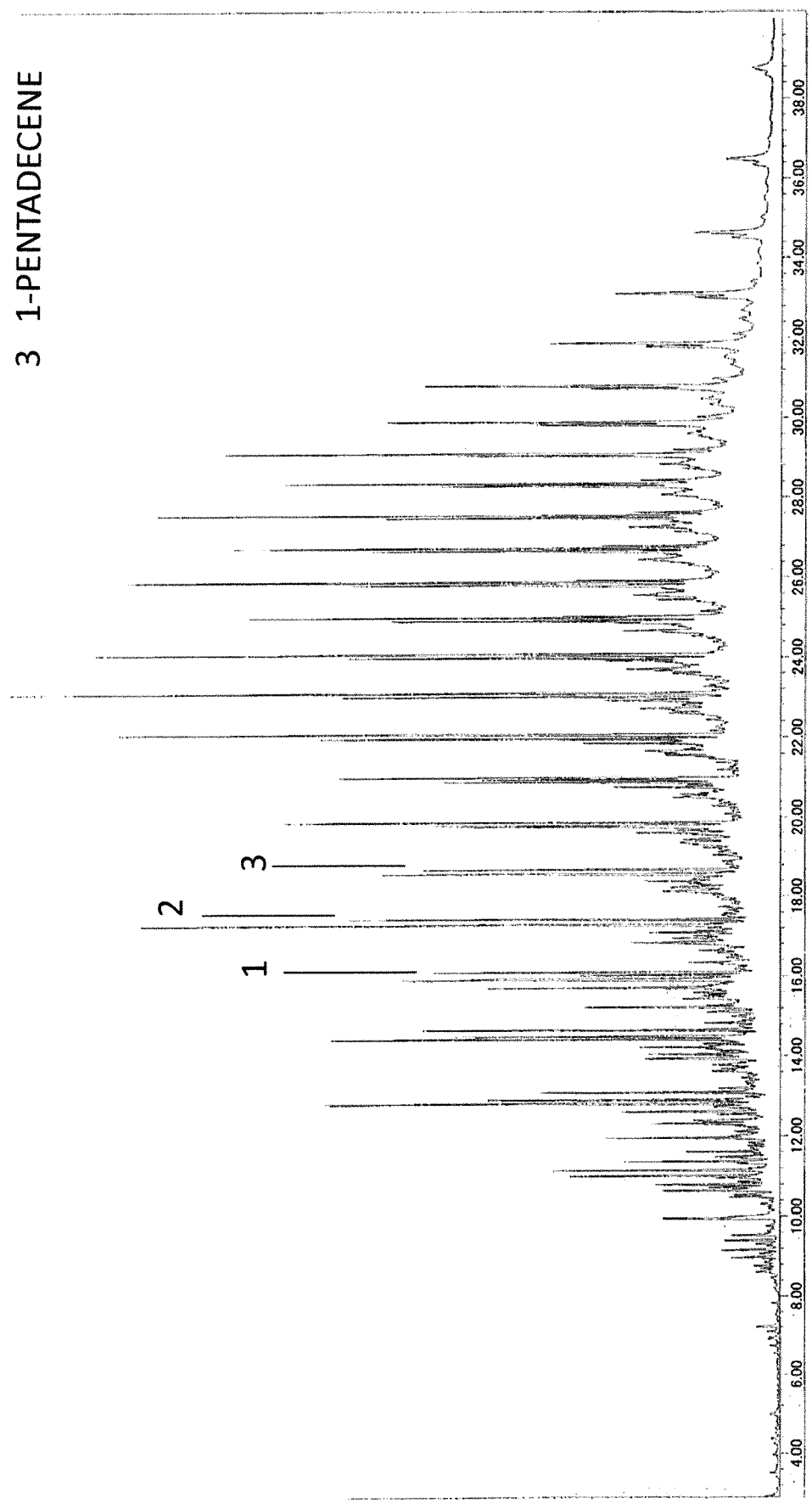
[FIGURE 2]

METHOD OF ANALYZING RESINS ADHERING TO CRUSHED POLYSILICON

This application is a U.S. national stage application of PCT/JP2017/044936 filed on 14 Dec. 2017 and claims priority to Japanese patent document 2016-244778 filed on 16 Dec. 2016, the entireties of which are incorporated herein by reference.

TECHNICAL FIELD

The present invention relates to a method of analyzing resins adhering to a surface of crushed polysilicon. More particularly, the present invention relates to an analysis method capable of qualitatively determining resins adhering to crushed polysilicon with high sensitivity and further capable of quantitatively determining the resins with high precision.

BACKGROUND ART

Polycrystalline silicon is used as an essential raw material for growing silicon single crystal for the production of semiconductor devices, etc., and requirements for its purity have been increasing.

Polycrystalline silicon is mainly produced by Siemens method. The Siemens method includes bringing a silane raw material gas such as trichlorosilane into contact with a heated silicon core rod to allow vapor phase epitaxy of polycrystalline silicon on the core rod surface. The polycrystalline silicon produced by the Siemens method is obtained in the form of a rod. This rod-like polycrystalline silicon has a size of a diameter of 80 to 150 mm and a length of 1000 mm or more. On this account, when this rod-like polycrystalline silicon is used in another step, for example, when it is used in facilities for growing silicon single crystal by CZ method, this polycrystalline silicon is cut into a rod of a prescribed length or crushed into appropriate lumps. These crushed polysilicon fragments are classified by a sieve or the like, when needed. Thereafter, in order to remove metal contaminants adhering to their surfaces, they are subjected to an etching step, for example, usually to a step of bringing the polycrystalline silicon into contact with hydrofluoric acid or an acidic solution containing hydrofluoric acid and nitric acid, and then subjected to a packaging step of filling them in a packaging bag of high purity, followed by shipping.

By the way, in the production process for the crushed polysilicon, not only various metal contaminants but also organic impurities may adhere to a surface of the crushed polysilicon. For example, in the above crushing step, handling is carried out using gloves made of a resin, such as polyvinyl chloride, nitrile rubber, polyethylene or polyurethane. Moreover, for a sieve to classify the polysilicon to obtain a prescribed size, polypropylene, polyethylene, polytetrafluoroethylene (PTFE), polyether ether ketone (PEEK) or the like is used.

In the etching step, for immersing the crushed polysilicon in an acidic solution containing hydrofluoric acid and nitric acid, a container made of a resin of high chemical resistance, such as polypropylene, polyethylene, PTFE or polyvinylidene fluoride (PVDF), is used.

Furthermore, in the packaging step, gloves made of a resin, such as polyvinyl chloride, nitrile rubber, polyethylene or polyurethane, are used. For the packaging bag, for example, polyethylene, polyethylene terephthalate or polypropylene is used. There is a possibility that these resins come into contact with the crushed polysilicon and adhere thereto.

Accordingly, if the resins adhering to the resulting crushed polysilicon can be identified, the contamination sources can be specified, and it becomes possible to make improvements to the contamination sources in order to prevent adhesion.

There is a method including heat-treating crushed polysilicon obtained by crushing a polycrystalline silicon rod, at a temperature of 350 to 600° C. in an inert gas atmosphere, introducing generated carbon dioxide into an infrared flow measuring cell and measuring the whole quantity of the adhering carbon (see Patent Document 1), though its problem to be solved differs from the present invention. Since this method is for determining the carbon quantity, the type of a resin and the quantity of an adhering resin cannot be specified.

On the other hand, in a method for purifying a surface of crushed polysilicon by heat-treating the crushed polysilicon in an inert gas atmosphere, an adsorbent was allowed to adsorb a gas generated at a heat treatment temperature of 180 to 350° C., then the adsorbent was heated, and a component desorbed was introduced into GC-MS (quadrupole mass spectrometry type gas chromatography) to carry out qualitative analysis of the component, and the results of this qualitative analysis have been reported (see Patent Document 2).

However, the results of the above qualitative analysis reveal that detection of a resin component adhering in a large quantity is easy but regarding a trace quantity of a resin component, there is room for improvement in detection sensitivity. In addition, since the above method is purification treatment of the crushed polysilicon that is a product, the heating temperature has an upper limit of 350° C., and no attention is directed to analysis of resins having decomposition starting temperatures exceeding the above temperature, such as fluororesin and PEEK that are highly likely to be used in the production process for polysilicon.

CITATION LIST

Patent Document

Patent Document 1: Japanese Unexamined Patent Application Publication No. 2013-170122
Patent Document 2: Japanese Unexamined Patent Application Publication No. 2016-56066

SUMMARY OF INVENTION

Technical Problem

The present invention has been made in the light of such a problem as above, and it is an object of the present invention to provide an analysis method capable of identifying the types of resins adhering to a surface of crushed polysilicon with high sensitivity, the types of the resins being unable to be grasped by the conventional technology, and further capable of determining the adhesion quantity of each of the resins with high precision, if needed.

Solution to Problem

In order to achieve the above object, the present inventors have earnestly studied. As a result, they have obtained the following knowledge. That is to say, the process for producing crushed polysilicon is carried out in an atmosphere in a clean room having a clean room filter with a PTFE film, and in general, resins such as polyvinyl chloride and epoxy are used for a bulkhead wall, a curtain, a partition and a flooring material of the clean room. In the resins, a plurality of additives, such as plasticizer, lubricant, solvent and colorant, are contained, and it is thought that among the additives, components having volatility (also referred to as organic volatile components hereinafter) are gradually released into the atmosphere at relatively low temperatures. Since the organic volatile components floating in the atmosphere cannot be removed by the filter, they adhere to a surface of crushed polysilicon. The present inventors have found that when the crushed polysilicon is heated to decompose the adhering resins and the resulting decomposition products are tried to be analyzed to identify the adhering resins, the organic volatile components volatilize at the same time and act as noise to thereby exert evil influence particularly on the identification of resins that adhere in trace quantities. Then, by removing the organic volatile components adhered to the crushed polysilicon surface, the present inventors have succeeded in high precision detection of decomposition products derived from the resins having adhered during the production process, and they have completed the present invention.

That is to say, the present invention provides an analysis method for organic impurities on a surface of crushed polysilicon, comprising removing organic volatile components from crushed polysilicon, then raising a temperature of the crushed polysilicon in a stream of an inert gas, collecting resin decomposition products produced at the heating temperature, and analyzing decomposition products unique to the resins, to thereby identify the types of the resins adhering to the crushed polysilicon.

In the present invention, in order to surely remove the organic volatile components, it is preferable to catty out the removal of the organic volatile components while maintaining the temperature at 180° C. or more and lower than the decomposition starting temperature of resins presumed to be brought into contact with polysilicon in a production process for the crushed polysilicon.

Moreover, it is preferable that the rise of the temperature of the crushed polysilicon after the removal of the organic volatile components be carried out stepwise, and the heating temperature is raised stepwise in the temperature range of not lower than the decomposition starting temperature of resins presumed to be brought into contact with polysilicon in the production process for the crushed polysilicon and not higher than 800° C. according to the resin decomposition starting temperatures of the resins, because the decomposition products unique to the adhering resins can be surely detected.

In addition, it is possible to prepare a standard curve regarding each of the decomposition products unique to the resins and to determine an adhesion quantity of each of the adhering resins based on the standard curve.

Advantageous Effects of Invention

According to the method of the present invention, the types of resins adhering to a surface of crushed polysilicon can be more precisely identified, and it becomes possible to accurately determine the adhesion quantity for each type of resins.

Accordingly, it becomes possible to accurately presume in which step of the production process for crushed polysilicon, contamination with resins has occurred, and further, how the degree of the contamination is, by the analysis of the resulting crushed polysilicon, and extremely important information on the management and improvement of the production process can be obtained.

BRIEF DESCRIPTION OF DRAWINGS

FIG. 1 is a chromatogram chart of organic volatile components by a GC/MS apparatus, the organic volatile components being evolved when crushed polysilicon is heated to 250° C.

FIG. 2 is a chromatogram chart of resin decomposition products by a GC/MS apparatus, the resin decomposition products being produced when polyethylene is heated from 250° C. to 450° C.

DESCRIPTION OF EMBODIMENTS (Crushed Polysilicon)

In the present invention, the crushed polysilicon that becomes an analysis object is obtained by crushing rod-like polycrystalline silicon produced by Siemens method, and includes any crushed polysilicon passed through the crushing step, typically any one of the following treatment steps including (a) crushing step, (b) etching step and (c) packaging step.

Of such crushed polysilicon, crushed polysilicon having passed through the packaging step that is a final step is preferably subjected to the analysis method of the present invention from the viewpoint of conduction of product management.

(a) Crushing Step:

Polycrystalline silicon is produced by Siemens method, fluidized bed method or the like, and since polycrystalline silicon produced by the Siemens method is usually obtained in the form of a rod, this rod-like polycrystalline silicon is cut as needed and then crushed into an appropriate size so that it can be easily introduced into, for example, a crucible for producing single crystal silicon. This crushing is carried out by, for example, crushing the polycrystalline silicon with a crushing machine such as jaw crusher or roll crusher or manually crushing it with a hammer or a chisel, whereby the polycrystalline silicon is processed into crushed polysilicon.

The shape of the crushed polysilicon obtained by the crushing is not particularly restricted, but a lump of indefinite shape (non-uniform surface state) obtained by crushing or the like is generally used. As the size of the crushed polysilicon, a particle diameter represented by a maximum length in a crushed fragment is generally 0.1 to 20 cm, preferably 1 to 10 cm. The crushed fragments may be those having sizes that are made uniform by a sieve or the like to adjust the particle diameter, when needed.

In the crushing step, the crushed silicon is liable to be brought into contact with a resin of a resin cover for a crushing machine, a resin cover for a crushing table, or the like and contaminated with the resin.

(b) Etching Step:

This step is a step of removing metals, oils, etc. adhering to the surface of the crushed polysilicon obtained in the crushing step, such adhesion occurring during crushing or handling, and thereby cleaning the crushed polysilicon, and known methods are adopted without any restriction. Examples of the etching steps include a pickling step using an acid solution and a subsequent water washing step using pure water. In the pickling step, a cleaning basket holding crushed polysilicon therein is immersed in a chemical tank containing an acid solution to dissolve the surface of the crushed polysilicon, whereby the contaminant is removed. The acid solution for use in the pickling step is, for example, a mixed solution of hydrofluoric acid and nitric acid. In the water washing step after the pickling step, it is preferable to use ultrapure water. The polycrystalline silicon washed with ultrapure water is preferably dried by air drying (through flow drying), and this drying is preferably carried out at a temperature of 80 to 150° C. for 0.5 to 24 hours.

In the etching step, the crushed silicon is liable to be brought into contact with a resin of a cleaning basket or a conveyor and contaminated with the resin.

(c) Packaging Step:

The packaging step is a step of filling crushed polysilicon into a resin packaging material, typically polyethylene, and also for the packaging, known methods are adopted without any restriction. For example, a method in which a packaging bag made of polyethylene is used and this bag is filled with crushed polysilicon manually or using a filling device can be mentioned. As the shape of the packaging bag, a shape of a flat bag, a gusset bag or the like is generally adopted, and a double bag structure in which the bag is doubled is preferably used. Alternatively, in a preferred embodiment, the inside of the package is depressurized or evacuated in order to suppress rubbing of the crushed polysilicon with the packaging material or to suppress fracture of the packaging material. Packaging in a double packaging bag may be carried out.

In the packaging step, the crushed silicon is liable to be brought into contact with a resin of a packaging material such as a packaging bag, gloves for inspection, or the like and contaminated with the resin.

The crushing step, the etching step and the packaging step are usually carried out in a clean room, but the crushed polysilicon is contaminated with volatile organic matters present in slight quantities in the clean room, such as additives released from a curtain, a flooring material, etc. made of polyvinyl chloride in the clean room.

(Analysis of Resins Adhering to Crushed Polysilicon)

The analysis method of the present invention is carried out by removing organic volatile components from the crushed polysilicon obtained in any one of the above steps, then raising the temperature of the crushed polysilicon in a stream of an inert gas, collecting resin decomposition products produced at the heating temperature, and analyzing decomposition products unique to the resins, to thereby identify the types of the resins adhering to the crushed polysilicon.

In the present invention, when the resins adhering to the crushed polysilicon are decomposed, it is extremely important to remove the organic volatile components in advance.

That is to say, by removing the organic volatile components in advance, noise due to the organic volatile components can be cancelled in the analysis of the decomposition products produced by the subsequent thermal decomposition of the adhering resins, and even regarding resins adhering in trace quantities, it becomes possible to surely detect their decomposition products.

It is preferable to carry out removal of the organic volatile components by heating under the temperature conditions where the adhering resins are not decomposed. Specifically, preferable is a method in which while maintaining the temperature at 180° C. or more and lower than the decomposition starting temperature of resins presumed to be brought into contact with polysilicon in the production process for the crushed polysilicon, the organic volatile components are evaporated and removed.

The organic volatile components are thought to be siloxanes and phthalic acid esters, and the heating temperature in the removal of these organic volatile components is preferably 180° C. or more in order to effectively remove the organic volatile components. Therefore, the organic volatile components in the present invention mean low-molecular weight compounds that vaporize at, for example, 250° C. or less and normal pressure. The upper limit of the heating temperature is set at a temperature lower than the decomposition starting temperature of a resin having a lowest decomposition temperature among resins that are presumed to adhere to the crushed polysilicon. Therefore, the heating temperature may be 300° C. or less, may be 280° C. or less, may be 250° C. or less, or may be 200° C. or less. When the temperature is low, a sufficient holding time is necessary in order to remove the organic volatile components. In the organic volatile components in the present invention, resin components are not included.

It is preferable to carry out heating for removing the organic volatile components in an atmosphere of an inert gas such as helium gas, argon gas or nitrogen gas, because combustion of the adhering resins is prevented. Of the inert gases, helium is most preferable.

As an apparatus used for heating for the removal of the organic volatile components, a furnace having a mechanism for heating the crushed polysilicon to a prescribed temperature and having a mechanism capable of steam extraction of the evaporated organic volatile components is used.

The steam extraction is preferably carried out using the aforesaid inert gas as a carrier gas. Specifically, a closed furnace equipped with a heating means such as an external heater or a high-frequency heating means and having a supply port for an inert gas and a gas exhaust port is preferably used.

The crushed polysilicon is stored in a container and set in the above furnace. The container is formed of a material that is stable at the heating temperature for carrying out removal of the organic volatile components, preferably even at the heating temperature for the decomposition of resins in the subsequent stage, for example, a heat-resistant ceramic such as quartz or alumina. As a matter of course, it is also possible to use the above material as a material of the furnace itself and to directly place the crushed polysilicon in the furnace. In either embodiment, it is preferable to carry out dummy heating of the container or the furnace in advance at a temperature not lower than the highest heating temperature in the analysis.

The apparatus of the above structure can be used also for heating for the decomposition of resins in the subsequent stage, and in general, after the removal of the organic volatile components is carried out, rise of the temperature to the resin decomposition temperature is continuously carried out.

In the present invention, the heating time for the removal of the organic volatile components is preferably a period of time by the end of which the organic volatile components substantially become non-existent in the gas having been extracted, and in general, a period of 30 to 100 minutes is suitable, and at 250° C., a period of not more than 60 minutes is enough and preferable. Through such heat treatment, 90% or more of the organic volatile components adhering to the crushed polysilicon are removed. In the present invention, as the removal ratio of the organic volatile components increases, the sensitivity is enhanced, and therefore, the organic volatile components are preferably removed in a ratio of 95% or more, more preferably 97% or more, and particularly preferably 99% or more. The removal ratio of the organic volatile components is determined by the following method. That is to say, a measurement sample collected from the crushed polysilicon is heated in the temperature range of 180° C. to a temperature lower than the resin decomposition temperature until the organic volatile components are not evolved, and the organic volatile components evolved during this time are adsorbed by an adsorbent. Thereafter, the adsorbent is heated, then desorbed components are measured by a GC/MS apparatus, and from the resulting chromatogram, peak areas of the organic volatile components are summed up to determine the peak area value ($A_{all}$) of all the organic volatile components adhering to the measurement sample. Subsequently, the same quantity of another measurement sample is collected from the crushed polysilicon, this sample is subjected to heat treatment (n hour(s)) for the removal of organic volatile components, then regarding the organic volatile components evolved during this time, the peak area value ($A_n$) of the organic volatile components removed by the heating is determined in the same manner as above, and from $A_n/A_{all}$, a removal ratio of the organic volatile components is determined.

In the above method, it is preferable that the time and the peak area value of the organic volatile components be recorded to prepare a standard curve for determining a peak area value of the organic volatile components at the arbitrary time for each heating temperature and that a removal ratio of the organic volatile components be estimated from the heating temperature and the heating time. In the actual operation, it is also possible to previously determine the conditions where any peak of the organic volatile components is not detected and to carry out removal of the organic volatile components according to the conditions.

FIG. 1 shows an example of a chromatogram chart obtained by heating crushed polysilicon to 250° C., allowing an adsorbent to adsorb organic volatile components evolved, then heating the adsorbent, and introducing the desorbed components into a GC/MS (quadrupole mass spectrometry type gas chromatography) apparatus to carry out qualitative analysis of the components. It can be seen from the chart that many types of organic volatile components are present on the crushed polysilicon surface.

In the present invention, the temperature of the crushed polysilicon from which the organic volatile components have been removed is then raised in a stream of an inert gas, and resin decomposition products produced at the heating temperature are collected.

The heating temperature is set at a temperature not lower than the decomposition starting temperature of resins presumed to be brought into contact with polysilicon in the production process for crushed polysilicon and lower than a temperature at which the resin decomposition products produced are not further modified. In general, the temperature is preferably stepwise set at a temperature higher than the decomposition starting temperature by 25 to 100° C.

For example, in the case where from the results of investigation of the production process for crushed polysilicon, resins shown in Table 1 below are given as examples of resins that are presumed to have a possibility of being brought into contact with crushed polysilicon in the production process, the decomposition starting temperatures of these resins are as shown in Table 1.

TABLE 1

| | Decomposition starting temperature of resin |
|---|---|
| Polypropylene | 300° C. |
| PVDF | 375° C. |
| Polyurethane | 300° C. |
| Polyethylene | 350° C. |
| PTFE | 560° C. |
| PEEK | 575° C. |

As described above, the heating temperature is appropriately determined according to the type and the resin decomposition temperature of each resin that is a measuring object, and by setting the heating temperature corresponding to each resin, high precision measurement becomes possible.

In order to accurately carry out quantitative determination, it is preferable to carry out heating at the above heating temperature until production of a decomposition product of a resin substantially ceases. It is preferable to properly determine this heating time by carrying out experiments in advance. According to the confirmation by the present inventors, the heating time is not less than 30 minutes, and in particular, a heating time of 60 minutes is enough.

In the present invention, the resin decomposition product obtained at the above heating temperature is recovered and collected as a gas, and the unique decomposition product contained in the gas is analyzed.

In the steam extraction of the resin decomposition product, the aforesaid inert gas is used as a carrier, the resin decomposition product is taken out as a gas, and the gas is collected by an adsorbent and subjected to analysis.

As the adsorbent used for collecting the decomposition product, an appropriate adsorbent can be used according to the resin that is an object. Specific examples of the adsorbents that may be used include, but are not limited to, polymer-based adsorbents, such as Tenax TA, carbon-based adsorbents, such as Carboxen 1000 (trade name, manufactured by Sigma-Aldrich Co. LLC) and Carbosieve SIII (trade name, manufactured by Sigma-Aldrich Co. LLC), and activated carbon. The adsorbent that adsorbs the organic volatile components and the adsorbent that adsorbs the resin decomposition products may be the same, and the adsorbent may be appropriately selected from the above-described adsorbents.

As the column, an appropriate column can be selected and used according to the resin to be measured. For example, a capillary column having a polysiloxane-based stationary phase, such as ZB-1MS (trade name, manufactured by Agilent Technologies), or a silica particle type PLOT column, such as GC-GasPro (trade name, manufactured by Phenomenex), can be used. The length of the column is sufficient length to separate the resin decomposition products, is more preferably 20 to 60 m, and is still more preferably not less than 30 m.

In the present invention, as method for desorbing the resin decomposition products from the adsorbent and analyzing them, known method can be adopted. For example, method wherein the adsorbent is heated, the desorbed decomposition products are concentration-collected by a cooled secondary adsorbent in a GC apparatus, and after heating of the secondary adsorbent, and the resin decomposition products are introduced into a column are generally used.

In the present invention, from the results of the analysis of the resin decomposition product obtained at the aforesaid each heating temperature, the type of the resin adhering to the crushed polysilicon is identified.

The following Table 2 shows decomposition products unique to typical resins. By checking the compound specified by the aforesaid analysis with the decomposition product unique to the following resin, the resin adhering to the crushed polysilicon can be identified. Also regarding other resins, decomposition tests are carried out in advance, whereby the adhering resins can be likewise identified from the decomposition products.

On the basis of the above results, the type of the resin investigated in the production process for crushed polysilicon and the location where the resin is present are specified, whereby the contamination source can be found, and proper improvements can be made to the contamination sources, that is, to the adhesion of the resin to the crushed polysilicon.

TABLE 2

| Type of resin | Decomposition product unique to resin |
| --- | --- |
| Polyethylene | straight-chain unsaturated hydrocarbon having 8 to 20 carbon atoms e.g., 1-tridecene, 1-tetradecene, 1-pentadecene |
| Polyurethane | 2-isocyanate-1,3-bis(1-methylethyl)benzene methylenebis(phenyl isocyanate) 1,6-dioxacyclododecane-7,12-dione |
| Polypropylene | 2,4-dimethyl-1-heptene 4,6-dimethyl-2-heptanone 4-isopropyl-1,3-cyclohexanedione |
| PTFE | tetrafluoroethylene hexafluoropropene cyclooctafluorobutane |
| PVDF | 1,3,5-trifluorobenzene 1,3-difluorobenzene vinylidene fluoride |
| PEEK | diphenyl ether, dibenzofuran, benzophenone |

According to the present invention, a decomposition product preferable for the quantitative determination of each resin is as follows: a preferred decomposition product of polyethylene is 1-pentadecene; that of polyurethane is 2-isocyanate-1,3-bis(1-methylethyl)benzene; that of polypropylene is 2,4-dimethyl-1-heptene; that of PTFE is hexafluoropropene, that of PVDF is 1,3,5-trifluorobenzene; and that of PEEK is diphenyl ether. Accordingly, it is preferable to prepare standard curves based on these decomposition products. In the working examples, standard curves were prepared based on these decomposition products.

In the analysis method of the present invention, in addition to the identification of the type of the resin adhering to the crushed polysilicon, measurement of its adhesion quantity is possible.

For example, regarding a characteristic decomposition product unique to each resin, a standard curve is prepared, and based on the standard curve, the quantity of the adhering resin can be determined in the following manner.

1) Regarding a resin that is a quantitative determination object, two or more of quantifiable amounts (generally 1 to 300 μg) of the resin, such as 10 μg, 100 μg and 200 μg, are weighed to prepare samples.

2) The resin sample is heated to a decomposition temperature of the resin in a helium atmosphere to decompose the whole quantity of the resin, and the whole quantity of the decomposition product is collected by a collecting agent.

3) The collecting agent is subjected to GC/MS analysis (GC conditions: e.g., column: ZB-1MS, carrier gas: He, flow rate: 1 mL/min, oven: 40° C. (maintained for 5 minutes) →10° C./min→280° C.; MS conditions: e.g., ion source temperature: 230° C., ionization mode: EI, ionization voltage: 70 eV), thereby obtaining a chart of a chromatogram.

FIG. 2 is an example of a chromatogram obtained by weighing 200 μg of polyethylene as a resin, allowing an adsorbent to adsorb resin decomposition products produced when the temperature is raised from 250° C. to 450° C., then heating the adsorbent, and measuring the desorbed components by a GC/MS apparatus.

5) From the chart of the chromatogram, a peak area value of a decomposition product characteristic of the resin is determined.

6) Resin samples different in weight are each subjected to the above measurement, and peak area values of decomposition products characteristic of the resins are determined.

7) A graph of "resin weight" and "peak area value of characteristic decomposition product" is made, and from a linear approximation having no intercept, a slope and $R^2$ are determined. $R^2$ is a coefficient of determination, and is utilized as an indicator of fitness of the linear approximation determined from the sampled value.

8) If $R^2$ is less than 0.9, the above operations are repeated while changing the weight of the resin sample to thereby increase plots until $R^2$ becomes not less than 0.9, and a standard curve is obtained.

(Confirmation of Accuracy of Quantitative Determination)

According to the method of the present invention, the types of resins adhering to a surface of crushed polysilicon can be identified with better sensitivity, and further, it becomes possible to accurately determine the adhering resin quantity for each type of resin, as described above. Then, in order to confirm accuracy of the quantitative determination, the following studies were carried out.

A rod-like polycrystalline silicon having a diameter of 150 mm and a length of 1000 mm produced by Siemens method was placed on a crushing table lined with silicon and crushed with a hammer made of tungsten carbide in a clean room, thereby obtaining crushed polysilicon containing 95 mass % of crushed fragments having a maximum length of 10 mm to 100 mm. For handling, gloves made of polyurethane were used. 20 Fragments of the resulting crushed polysilicon weighing about 500 g were taken out, and as a resin for the crushed fragments, polyethylene chips were further weighed so that the weight became 100 ppbw based on the weight of the crushed polysilicon, and held together with the crushed polysilicon in a quartz chamber in a heating apparatus.

The crushed polysilicon including the polyethylene chips was heated at 250° C. to eliminate organic volatile components, then the temperature was raised from 250° C. to 450° C., a resin decomposition product produced during the temperature rise was adsorbed by an adsorbent, thereafter the adsorbent was heated, and a component desorbed by the heating was measured with a GC/MS apparatus. For comparison, the crushed polysilicon including the polyethylene chips was directly heated to 450° C. without eliminating organic volatile components, a resin decomposition product produced during the temperature rise was adsorbed by an adsorbent, thereafter the adsorbent was heated, and a component desorbed by the heating was measured with a GC/MS apparatus. In order to confirm reproducibility, these operations were carried out 5 times under the respective conditions.

From the resulting peak area, quantitative determination of the adhering polyethylene was carried out using a previously prepared standard curve, and as a result, it was confirmed that with regard to each of the samples from which organic volatile components had been eliminated, the quantity of polyethylene was highly precisely determined as 90 to 110 ppbw. With regard to each of the samples having not been subjected to elimination of organic volatile components, a peak unique to the polyethylene was confirmed, but there were some samples in which polyethylene peak was not able to be isolated because a peak of an organic volatile component overlapped. In addition, the value determined widely varied to be 90 to 300 ppbw.

As described above, by the method of the present invention, the type of the resin adhering to the surface of the crushed polysilicon was identified with better sensitivity, and it became possible to accurately determine the adhering resin quantity for each type of resin.

The present invention is summarized as follows.

(1) An analysis method for impurities on a surface of crushed polysilicon, comprising removing organic volatile components from crushed polysilicon, then raising a temperature of the crushed polysilicon in a stream of an inert gas, collecting resin decomposition products produced at the heating temperature, and analyzing decomposition products unique to the resins, to thereby identify the types of the resins adhering to the crushed polysilicon.

(2) The analysis method according to (1), wherein the removal of the organic volatile components is carried out while maintaining the temperature at 180° C. or more and lower than the decomposition starting temperature of resins presumed to be brought into contact with polysilicon in a production process for the crushed polysilicon.

(3) The analysis method according to (1) or (2), wherein the rise of the temperature of the crushed polysilicon is carried out stepwise according to the resin decomposition starting temperature.

(4) The analysis method according to any one of (1) to (3), wherein regarding each of the decomposition products unique to the resins, a standard curve is prepared, and based on the standard curve, an adhesion quantity of each of the adhering resins is determined.

In addition, the present invention can also be described as below.

(5) An analysis method for impurities on a surface of crushed polysilicon, comprising:

obtaining crushed polysilicon having organic volatile components and resins adhering to its surface, removing the organic volatile components from the crushed polysilicon, heating the crushed polysilicon in a stream of an inert gas to decompose the adhering resins, collecting the resin decomposition products, analyzing decomposition products unique to the resins, and identifying the types of the resins adhering to the crushed polysilicon.

EXAMPLES

The present invention will be described with reference to the following examples, but the present invention is in no way limited to those examples.

In the examples, a heating apparatus and an analysis apparatus described below were used.

1) Heating Apparatus

As a heating apparatus, a muffle furnace to which a gas flow channel was connected was used. As a container for storing crushed polysilicon therein, a quartz container was used. As an adsorbent, Tenax TA that was a polymer-based adsorbent was used for collecting decomposition products of polyethylene, polyurethane, polypropylene and PEEK. For collecting decomposition products of PTFE and PVDF, Carboxene 1000 was used. Heating aiming at removal of organic volatile components was carried out at a heating temperature of 250° C., and this heating temperature was maintained for 49 minutes. Heating aiming at decomposition of adhering resins was carried out at 400 to 650° C., and the temperature described in each example mentioned later was maintained for 49 minutes. As a carrier gas, helium was passed through at a flow rate of 100 mL/min. The heating conditions are summarized in Table 3 below.

TABLE 3

| | |
|---|---|
| Heating apparatus | Muffle Furnace FP300 (trade name, manufactured by Yamato Scientific Co., Ltd.) |
| Quartz container | ID 150 mm × L 100 mm |
| Adsorbent 1 | Tenax TA (100 mg) |
| Adsorbent 2 | Carboxene 1000 (100 mg) |
| Organic volatile component removal temperature | ordinary temperature → 250° C. (23° C./min), maintained for 49 minutes |
| Heating collection temperature | 250° C. → 400 to 650° C. (23° C./min), maintained for 49 minutes |
| Carrier gas | Helium (purity: not less than 99.99995%) |
| Carrier gas flow rate | 100 mL/min |

2) Analysis Apparatus

As an analysis apparatus, quadrupole mass spectrometry type GC/MS was used. As an analytical column for decomposition products of polyethylene, polyurethane, polypropylene and PEEK, a siloxane polymer type general capillary column ZB-1MS was adopted. As an analytical column for decomposition products of PTFE and PVDF, a silica particle type PLOT column GC-GasPro that was excellent in isolation of low-boiling point components was adopted because the decomposition products were low-boiling point compounds. The analysis conditions are summarized in Table 4 below.

TABLE 4

| | |
|---|---|
| Apparatus | GC/MS (quadrapole mass spectrometry type gas chromatography) |
| Column 1 | ZB-1MS (ID 0.25 mm × L 30 m) |
| Column 2 | GC-GasPro (ID 0.32 mm × L 30 m) |
| Carrier gas/flow rate | Helium (purity: not less than 99.99995%) |
| Carrier gas flow rate | 1.0 to 2.0 mL/min |
| Mass spectrometry detector | EI mode |

Example 1

In a crushing step, rod-like polycrystalline silicon having a diameter of 150 mm and a length of 1000 mm produced by Siemens method was placed on a crushing table lined with silicon, and crushed with a hammer made of tungsten carbide, thereby obtaining crushed polysilicon containing 95 mass % of crushed fragments having a maximum length of 10 mm to 110 mm. For handling, polyethylene gloves were used.

In an etching step, 5 kg of the resulting crushed polysilicon was introduced into a cleaning basket of PVDF, then immersed in a mixed solution of hydrofluoric acid and nitric acid (ratio by volume: 1:20) for 5 minutes, thereafter immersed in ultrapure water for 30 minutes, and dried at 80° C. for 24 hours. Thereafter, in a clean booth, the resulting crushed polysilicon was placed on a workbench lined with silicon, and packaged in a polyethylene packaging bag using polyethylene gloves.

From the packaging bag, arbitrary 20 fragments of crushed polysilicon having a maximum length of 10 mm to 30 mm and weighing about 500 g were taken out using polyethylene gloves, and they were held in a quartz chamber in the heating apparatus. The crushed polysilicon fragments were heated at 250° C. in an atmosphere of helium gas flowing at a flow rate of 100 mL/min, and held for 49 minutes, followed by eliminating organic volatile components generated. Thereafter, the heating temperature was maintained at 400° C. for 49 minutes. From an area of each resin decomposition product produced, a resin adhesion quantity was calculated using a standard curve prepared in advance. The results are set forth in Table 5.

Example 2

Operations were carried out under the same conditions as in Example 1, except that in the etching step, the material of the cleaning basket was changed to polypropylene. The results are set forth in Table 5.

Example 3

Operations were carried out under the same conditions as in Example 1, except that in the etching step, the material of the cleaning basket was changed to PTFE, and the heating temperature was maintained at 400° C. for 49 minutes and then further maintained at 650° C. for 49 minutes. The results are set forth in Table 5.

Example 4

Operations were carried out under the same conditions as in Example 1, except that in the crushing step, the material of the gloves for handling was changed to polyurethane. The results are set forth in Table 5.

Example 5

Operations were carried out under the same conditions as in Example 1, except that in the crushing step, after the crushing with a hammer, the crushed fragments having a maximum length of 10 mm to 110 mm were classified to obtain crushed fragments having a maximum length of 10 mm to 30 mm by a sieve made of PEEK, and the heating temperature was maintained at 400° C. for 49 minutes and then further maintained at 650° C. for 49 minutes. The results are set forth in Table 5.

Example 6

Operations were carried out under the same conditions as in Example 1, except that after the polycrystalline silicon was crushed with a hammer to obtain crushed polysilicon containing 95 mass % of crushed fragments having a maximum length of 10 mm to 110 mm, the etching step was not carried out, and the crushed fragments were manually introduced into a polyethylene packaging bag directly. The results are set forth in Table 5.

Comparative Example 1

In this comparative example, crushed polysilicon having passed through the crushing step, the etching step and the packaging step described in Example 1 was held in a quartz chamber in the heating apparatus, then without carrying out an operation of removal of organic volatile components, the crushed polysilicon was kept at 400° C. for 49 minutes in an atmosphere of helium gas flowing at a flow rate of 100 mL/min, and then, resin decomposition products produced were collected and an analysis chart was obtained in the same manner as in Example 1. However, as shown in Table 5, the peak of decomposition product of polyethylene was unable to be isolated because its peak and a peak of an organic volatile component overlapped, and accurate quantitative determination was unable to be carried out. Moreover, a peak of PVDF was unable to be detected because it was buried in noise.

TABLE 5

|  | Polyethylene | Polyurethane | Polypropylene | PVDF | PTFE | PEEK |
| --- | --- | --- | --- | --- | --- | --- |
| Ex. 1 | 340 ppbw | <1 ppbw | <2 ppbw | 11 ppbw | <0.5 ppbw | <0.4 ppbw |
| Ex. 2 | 164 ppbw | <1 ppbw | 63 ppbw | <0.3 ppbw | <0.5 ppbw | <0.4 ppbw |
| Ex. 3 | 278 ppbw | <1 ppbw | <2 ppbw | <0.3 ppbw | 54 ppbw | <0.4 ppbw |
| Ex. 4 | 43 ppbw | 13 ppbw | <2 ppbw | 2 ppbw | <0.5 ppbw | <0.4 ppbw |
| Ex. 5 | 106 ppbw | <1 ppbw | <2 ppbw | 9 ppbw | <0.5 ppbw | 44 ppbw |
| Ex. 6 | 391 ppbw | <1 ppbw | <2 ppbw | <0.3 ppbw | <0.5 ppbw | <0.4 ppbw |
| Comp. Ex. 1 | impossibility in accurate determination |  |  | not detected |  |  |

The invention claimed is:

1. A method for analyzing impurities on a surface of crushed polysilicon, comprising:
    removing organic volatile components from crushed polysilicon,
    raising a temperature of the crushed polysilicon in a stream of an inert gas,
    collecting resin decomposition products produced at a temperature not lower than a decomposition starting temperature of resins presumed to be brought into contact with polysilicon in a production process for the crushed polysilicon and lower than a temperature at which the resin decomposition products are not further modified, and
    analyzing decomposition products unique to the resins, to thereby identify the types of the resins adhering to the crushed polysilicon.

2. The method according to claim 1, wherein the removing of the organic volatile components is carried out while maintaining a temperature at 180° C. or more and lower than the decomposition starting temperature of resins presumed to be brought into contact with polysilicon in a production process for the crushed polysilicon.

3. The method according to claim 1, wherein the raising of the temperature of the crushed polysilicon is carried out stepwise according to the resin decomposition starting temperature.

4. The method according to claim 1, wherein regarding each of the decomposition products unique to the resins, a standard curve is prepared, and based on the standard curve, an adhesion quantity of each of the adhering resins is determined.

5. The method according to claim 2, wherein the raising of the temperature of the crushed polysilicon is carried out stepwise according to the resin decomposition starting temperature.

6. A method for analyzing impurities on a surface of crushed polysilicon, comprising:
   providing crushed polysilicon having resins adhered to a surface of the crushed polysilicon;
   removing organic volatile components from the crushed polysilicon at a temperature where the adhered resins are not decomposed;
   raising the temperature of the crushed polysilicon in a stream of an inert gas;
   collecting resin decomposition products at a temperature not lower than a decomposition starting temperature of the adhered resins and lower than a temperature at which the resin decomposition products are not further modified; and
   analyzing the resin decomposition products to identify the types of the resins adhered to the crushed polysilicon.

* * * * *